(12) United States Patent
Guyon et al.

(10) Patent No.: US 8,765,160 B2
(45) Date of Patent: Jul. 1, 2014

(54) METHODS FOR CONTROL OF SOIL-DWELLING PESTS AND/OR SOIL-BORNE DISEASES

(75) Inventors: Frederique Guyon, Muenchwilen (CH); Christoph Grimm, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 1436 days.

(21) Appl. No.: 12/067,370

(22) PCT Filed: Sep. 18, 2006

(86) PCT No.: PCT/EP2006/009051
§ 371 (c)(1),
(2), (4) Date: Mar. 19, 2008

(87) PCT Pub. No.: WO2007/039080
PCT Pub. Date: Apr. 12, 2007

(65) Prior Publication Data
US 2008/0206345 A1 Aug. 28, 2008

(30) Foreign Application Priority Data

Sep. 19, 2005 (EP) .................................... 05020337

(51) Int. Cl.
| | | |
|---|---|---|
| *A01N 25/14* | (2006.01) | |
| *A01N 25/02* | (2006.01) | |
| *A01N 25/04* | (2006.01) | |
| *A01N 25/08* | (2006.01) | |
| *A01N 25/12* | (2006.01) | |
| *A01N 43/16* | (2006.01) | |
| *A01N 47/34* | (2006.01) | |

(52) U.S. Cl.
CPC ............... *A01N 25/14* (2013.01); *A01N 25/02* (2013.01); *A01N 25/04* (2013.01); *A01N 25/08* (2013.01); *A01N 25/12* (2013.01); *A01N 43/16* (2013.01); *A01N 47/34* (2013.01); *Y10S 47/09* (2013.01)
USPC ........... 424/417; 424/400; 424/405; 424/409; 424/489; 514/30; 514/450; 514/594; 47/57.6; 47/DIG. 9

(58) Field of Classification Search
CPC ....... A01N 25/02; A01N 25/12; A01N 25/14; A01N 43/04; A01N 43/16; A01N 43/08
USPC .................................... 514/30, 269, 422, 538
See application file for complete search history.

(56) References Cited

U.S. PATENT DOCUMENTS

| | | | |
|---|---|---|---|
| 2009/0124499 A1* | 5/2009 | Baum et al. ................... | 504/100 |
| 2010/0173776 A1* | 7/2010 | Schade et al. ................. | 504/227 |

FOREIGN PATENT DOCUMENTS

| | | |
|---|---|---|
| WO | 03/024222 A | 3/2003 |
| WO | 03/069991 A | 8/2003 |
| WO | 2005/089545 A | 9/2005 |
| WO | 2005/089546 A | 9/2005 |
| WO | 2005/094155 A | 10/2005 |
| WO | 2005/094585 A | 10/2005 |

OTHER PUBLICATIONS

Fischer, S.A., et al.: "Environmental Concentrations and Aquatic Toxicity Data on Diflubenzuron Dimilin", Critical Reviews in Toxicology, vol. 22, No. 1, 1992, pp. 45-79.

Mulder, R., et al.: "The Laboratory Evaluation of 2 Promising New Insecticides Which Interfere With Cuticle Deposition", Pesticide Science, vol. 4, No. 5, 1073, pp. 737-745, 1973.

* cited by examiner

*Primary Examiner* — Neil Levy
(74) *Attorney, Agent, or Firm* — Brian D. McAlhaney

(57) ABSTRACT

A method for the control of soil-dwelling pests and/or soil-borne diseases comprising treating a plant propagation material with an effective amount of the pesticidal composition and/or applying an effective amount of a pesticidal composition to a locus where control is desired, provided that the composition comprises, as active ingredient, one or more pesticides (A) having a water solubility of at most 100 μg/liter, at 25° C. at neutral pH, and at least one formulation auxiliary, wherein the size of particles in the composition is in the range 3.60 μm to 0.70 μm at $X_{90}$. Abamectin has been found to be particularly effective against nematode damage.

15 Claims, No Drawings

METHODS FOR CONTROL OF SOIL-DWELLING PESTS AND/OR SOIL-BORNE DISEASES

This application is a 371 of International Application No. PCT/EP2006/009051 filed Sept. 18. 2006, which claims priority to EP 05020337.1 filed Sept. 19, 2005, the contents of which are incorporated herein by reference.

The present invention relates to methods of protecting plant propagation material, especially seeds, and plant organs that grow at a later point in time, methods for the control of soil-dwelling pests and/or soil-borne diseases, methods for improving the growing characteristics of plants, and pesticidal compositions and pesticides for use in such methods.

Soil-dwelling pests and/or soil-borne diseases in horticultural and agricultural practices are difficult to detect because of low damaging populations (e.g. soil insects), their microscopic size, (eg. fungal pathogens, nematodes) and because of resting stages that differ from the active stage (e.g. fungal pathogens). Treatment during crop growth is almost impossible. Some plants are produced underground (e.g. potatoes, carrots) and growers seek to limit direct impact of damaging organisms on yield and quality; also long-term plants (e.g. vines, tree crops) may decline in productivity over time as noxious organisms infest the root zone.

In the more intensive production systems this usually meant the use of broad-spectrum soil fumigants such as methyl bromide and metham sodium. Methyl bromide is now being phased out under the Montreal Protocol.

For these reasons, soil-borne pests represent the most difficult pest management situation in the growing of a plant.

Owing to the unpredictable and cryptic nature of many soil pests, and their capacity to cause damage even when present in low numbers, growers generally counter the threat of soil-borne pests and diseases with prophylactic applications of pesticides, the choice of which depends on the perceived need in relation to what experience has shown to be the major local pest. In recent times, the application of relatively specific pesticides (i.e. insecticides, fungicides, bactericides, nematicides) is giving way to the use of broad-spectrum soil fumigant, such as methyl bromide and metham sodium. Methyl bromide is now being phased out under the Montreal Protocol. Metham sodium produces the toxic compound methyl isothiocyanate (MITC) upon contact with moist soil. While referred to as a soil fumigant, which implies that the pesticide moves through the soil as a gas, metham sodium is probably more accurately described as a soil pesticide as the MITC is highly water soluble and primarily disperses in the soil moisture. Despite its widespread and increasing use in horticulture generally, and intensive use in some potato producing regions, many growers do not use metham sodium because of prohibitive cost. Also, growers are often concerned about using such a powerful broad-spectrum pesticide for safety or environmental reasons. Based on adverse past experiences, there are also concerns about becoming reliant on a single pesticide. In the case of soil fumigants, there is an extremely limited and shrinking choice and no new products on the horizon.

It has now been found that certain pesticides (or active ingredient compounds), especially insecticides, acaricides, fungicides, bactericides and nematicides having a defined particle size provides improved control of soil-dwelling pests and/or soil-borne diseases and accordingly protect plant propagation material and plant organs that grow at a later point in time against damage from soil-dwelling pests and/or soil-borne diseases. The pesticide in a suitable form can be treated onto the plant propagation material before or during the planting or sowing of the propagation material, and/or can be applied directly to the locus of the plant propagation material before, during or after the planting or sowing of the propagation material. This will offer growers a more soundly-based option to gain the best possible benefits in soil-dwelling pest and/or soil-borne disease suppression.

Therefore, in a first aspect the present invention provides a method of protecting plant propagation material and plant organs that grow at a later point in time, which comprises treating the plant propagation material with an effective amount of a pesticidal composition comprising, as active ingredient, one or more pesticides (A) having a water solubility of at most 100 µg/liter at 25° C. at neutral pH, and at least one formulation auxiliary, wherein the size of particles in the composition is in the range 3.60 µm to 0.70 µm.

The present invention, accordingly, protects a plant propagation material and plant organs that grow at a later point in time against damage or injury from soil-dwelling pests and/or soil-borne diseases. The protection against seed-borne diseases is also be achieved. In such circumstances, the growing characteristics of the plant are improved.

In a second aspect the present invention provides a method for the control of soil-dwelling pests and/or soil-borne diseases comprising treating a plant propagation material with an effective amount of the pesticidal composition and/or applying an effective amount of a pesticidal composition to a locus where control is desired, provided that the composition comprises, as active ingredient, one or more pesticides (A) as defined in the first aspect, and at least one formulation auxiliary, wherein the size of particles in the composition is in the range 3.60 µm to 0.70 µm.

In a third aspect the present invention provides a pesticidal composition comprising, as active ingredient, one or more pesticides (A) as defined in the first aspect, and at least one formulation auxiliary, wherein the size of particles in the composition is in the range 3.60 µm to 0.70 µm.

In a fourth aspect the present invention provides a pesticide as defined in the first aspect having a particle size in the range 3.60 µm to 0.70 µm.

The invention is described in more detail below.

Generally the pesticide (A) according to the present invention has poor water solubility for example at most 100, such as less than 50, preferably between 20 and 1, more preferably in the range of 10 to 1, µg/liter, at 25° C. at neutral pH, for example, as indicated in the Pesticide Manual), and so compositions comprising pesticide (A) typically contain pesticide (A) as suspended solid particles, pesticide (A) in a capsule or pesticide (A) in an, for example, oil in water, emulsion droplet. The pesticides are therefore generally more soluble in organic solvents or dispersible therein. A surprising finding of the present invention is that the pesticidal activity of such pesticides is improved upon treatment or application of the pesticide (A), e.g., in the form of a pesticidal composition, according to the present invention.

The pesticide or active ingredient compound can be in free or salt form.

Suitable examples of pesticide (A) are abamectin, acrinathrin, alpha-cypermethrin, acequinocyl, amitraz, benomyl, beta-cyfluthrin, bifenthrin, bioresmethrin, bistrifluron, bromopropylate, chlorethoxyfos, chlorfluazuron, clofentezine, cyfluthrin, cyhalothrin, cypermethrin, cyphenothrin, dodemorph, esfenvalerate, etofenprox, fenvalerate, flucycloxuron, flufenoxuron, hydramethyinon, lambda-cyhalothrin, lufenuron, mecarbam, novaluron, permethrin, phenothrin, silafluofen, tau-fluvalinate, ZXI 8901 (3-(4-bromophenoxy)-a-cyanobenzyl 2-[4-(difluoromethoxy)phenyl]-3-methylbutanoate), and certain bisamides, such as flubendiamide (3-iodo-N'-(2-mesyl-1,1-dimethylethyl)-N-{4-[1,2,2,2-tetrafluoro-1-(trifluoromethyl)ethyl]-o-tolyl}phthalamide) and a compound of formula A-1:

A1

In an embodiment, abamectin, lambda-cyhalothrin, cyfluthrin, beta-cyfluthrin, esfenvalerate, silafluofen, tau-fluvalinate, etofenprox, fenvalerate, cyhalothrin, alpha-cypermethrin, cypermethrin, novaluron, lufenuron, flufenoxuron, mecarbam, ZXI 8901, benomyl, flubendiamide and a compound of formula A-1 are preferred examples of pesticide (A).

In a preferred embodiment, abamectin is pesticide (A).

The size of the particles of any one of the aspects of the invention is preferably in the range of 3.40 μm to 0.80 μm, more preferably 2.60 μm to 1.2 μm, most preferably 2.00 μm to 1.50 μm.

The specific optimum size for the pesticide generally varies depending on the actual pesticide, and the pesticidal composition comprising it, i.e., whether the pesticide is present as a suspended solid or in dispersed capsule or in an emulsion droplet. The pesticide particle, may, therefore, exist as a suspended solid or as a dispersed capsule or as an emulsion droplet (e.g., oil in water droplet), and accordingly particle size herein defined refers to such a particle.

The particle size as used herein refers to the diameter of the particle. Generally a compound or sample has a plurality of particles of different sizes, such that the particle size of the compound or sample is a distribution. The particle size as used herein, unless otherwise specifically stated, refers to the maximum size that 90 volume % of the particles in the compound or sample have, i.e., the size corresponds to the largest size of 90 volume % of the smallest particles (often referred to as $x_{90}$; see method ISO 13320-1:1999 for further details). Devices and methods for determining the particle size of pesticides are known to a skilled person. Examples of suitable devices are Malvern Mastersizer S, CILAS, COULTER COUNTER, Helos (SYMPATEC).

In an embodiment, the particles in the compound or sample having a size defined herein as corresponding to $x_{90}$ also have a size at $x_{50}$, i.e. 50 volume % of the smallest particles in the sample or compound have a certain maximum size (see method ISO 13320-1:1999 for further details). Accordingly, table below provides the particle size correspondence between $x_{90}$ and $x_{50}$:

| $x_{90}$ | $x_{50}$ |
|---|---|
| 3.60 μm | 1.44 μm |
| 3.40 μm | 1.40 μm |
| 2.60 μm | 1.16 μm |

-continued

| $x_{90}$ | $x_{50}$ |
|---|---|
| 2.00 μm | 0.95 μm |
| 1.50 μm | 0.75 μm |
| 1.20 μm | 0.55 μm |
| 0.80 μm | 0.50 μm |
| 0.70 μm | 0.44 μm |

Generally the pesticides are available for use in pesticidal compositions which comprise the pesticides and at least one formulation auxiliary, wherein one or more auxiliaries may be incorporated into the pesticide particle by its use in capsules or emulsion droplets, or be suspended with the pesticide in the composition. Therefore, the pesticide particle size refers to the pesticide containing particles. In the event that non-pesticide particles are also in the composition, such as a pigment, that are detected as particles in the composition, the particle size defined herein can also refer to the particle size of the sum of the particles in the composition (including non-pesticide particles). Preferably, the particle size is the pesticide particle size.

Preferably the pesticide particle is a suspended solid particle, generally in an aqueous composition.

In an embodiment the particle size is the actual size of the pesticide or active ingredient compound.

In an embodiment the particle size for abamectin is in the range 3.40 μm to 0.80 μm, more preferably 2.60 μm to 1.2 μm, most preferably 2.00 μm to 1.50 μm (each based on $x_{90}$), and the particles are suspended in an aqueous composition.

The defined pesticide particles are especially effective on soils of the type sandy clay, sandy clay loam, sandy loam, loamy sand or sand, such as soils that contain one or more of sand, clay and silt in a proportion of 45-100% sand, 0-55% clay and/or 0-50% silt, and as a result of the improved pest control a particular advantage is that lower amounts of the pesticide may be used.

Methods for achieving stable particle sizes for particles, especially pesticide particles, are known to a skilled person.

A skilled person would need to ensure that the particle size achieved for a pesticide is stable and that the pesticide particles are not prone to sedimentation, aggregation or precipitation in the pesticidal compositions leading to unsatisfactory pesticidal compositions. Methods for achieving this are known, for example, by choosing a suitable surfactant in an appropriate amount.

In the case of solid pesticide particles, air-jet milling and dry milling are suitable methods of sizing particles. Also appropriate is precipitation of the particles under controlled conditions so that a pre-determined particle size range is obtained. In the case the particles are suspended in a liquid, wet milling is a suitable method of sizing the particles. Generally, one would mill the solid particles of a pesticide, such as the technical material thereof, to a pre-determined particle size and then suspend the milled particles in a liquid, such as water, and then complete milling via wet milling to achieve the desired particle size.

It is known in the art how to make capsules or emulsion droplets to a desired size. For example, a pesticidal composition having defined emulsion droplets size can be achieved by suitable agitation of organic and aqueous compositions (one of which comprise the pesticide & suitable surfactant(s)), and/or by using the pesticidal composition with a particular device, such a nozzle, equipped with features to control the particle size. Such methods and devices are known to a skilled person.

The present invention is especially suitable for agromically important plants, which refers to a plant that is harvested or cultivated or grown on a commercial scale.

Examples of such agronomic plants (or crops) include, without limitation, cotton, corn, cereals (including wheat, barley, rye, and rice), vegetables (including fruiting vegetable, such as tomatoes, bulb vegetables, leafy vegetables, brassicas and vegetable roots), clovers, legumes (including beans, soybeans, peas and alfalfa), sugar cane, sugar beets, tobacco, rapeseed (canola), fruits (such as bananas, cherries, oranges, lemons, grapefruit, mandarins, citrus, grapes, stone fruits), perennial crops, deciduous plants, sunflower, safflower, and sorghum.

Preferred examples are wheat, barley, rye, rice, cotton, maize, soya beans, oilseed rape, fruiting vegetable, such as tomatoes, bulb vegetables, leafy vegetables, brassicas and vegetable roots, potatoes, sunflowers, sugar beet and sorghum.

The plants used according to the invention and propagation material thereof, can be genetically modified in that they contain one or more genes expressing pesticidal resistance, such as insect, nematode, herbicide and disease resistances.

They may be transformed by means of recombinant DNA technology in such a way that they are—for instance—capable of synthesizing selectively acting toxins as are known, for example, from toxin-producing invertebrates, especially of the phylum Arthropoda, as can be obtained from Bacillus thuringiensis strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The term "plant propagation material" is understood to denote all the generative parts of the plant, such as seeds, which can be used for the multiplication of the latter and vegetative plant materials such as cuttings and tubers (for example, potatoes). Accordingly, as used herein, part of a plant includes propagation material. There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Parts of plant and plant organs that grow at later point in time are any sections of a plant that develop from a plant propagation material, such as a seed. Parts of plant, plant organs, and plants can also benefit from the pathogenic and/or pest damage protection achieved by the application of a pesticidal composition on to the plant propagation material. In an embodiment, certain parts of a plant and certain plant organs that grow at later point in time can also be considered as plant propagation material, which can themselves be applied (or treated) with the pesticidal composition; and consequently, the plant, further parts of the plant and further plant organs that develop from the treated parts of plant and treated plant organs can also benefit from the pathogenic and/or pest damage protection achieved by the application of the pesticidal composition on to the certain parts of plant and certain plant organs.

The term "plant propagation material" is understood to denote all the generative parts of the plant, such as seeds, which can be used for the multiplication of the latter and vegetative plant material such as cuttings and tubers (for example, potatoes). There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. A preferred plant propagation material is the seed. In an aspect of the present invention, these young plants and generative parts may be protected before transplantation by a total or partial treatment, for example, by treatment, for example by immersion, by a pesticide, e.g. in the form of a pesticidal composition, according to the present invention.

The present invention is especially effective against soil-dwelling or inhabiting pests, such as animal pests (in particular insects, arachnids and nematodes) and soil-borne fungal pathogens, which are found in agriculture, in horticulture and in forestry, and can damage the plant in the early stages of plant development.

Examples Animal Pests Include:

from the order Lepidoptera, for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia* spp., *Cryptophlebia leucotreta*, *Crysodeixis includens*, *Cydia* spp., *Diatraea* spp., *Diparopsis castanea*, *Earias* spp., *Elasmopalpus* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Coleoptera, for example, *Agriotes* spp., *Anthonomus* spp., *Atomaria linearis*, *Ceutorhynchus* spp., *Chaetocnema tibialis*, *Cosmopolites* spp., *Curculio* spp., *Dermestes* spp., *Diabrotica* spp., *Epilachna* spp., *Eremnus* spp., *Gonocephalum* spp., *Heteronychus* spp., *Leptinotarsa decemlineata*, *Lissorhoptrus* spp., *Melolontha* spp., *Orycaephilus* spp., *Otiorhynchus* spp., *Phlyctinus* spp., *Phyllotreta* spp., *Popillia* spp., *Protostrophus* spp., *Psylliodes* spp., *Rhizopertha* spp., *Scarabeidae*, *Sitophilus* spp., *Sitotroga* spp., *Tenebrio* spp., *Tribolium* spp. and *Trogoderma* spp.;

from the order Orthoptera, for example, *Blatta* spp., *Blattella* spp., *Gryllotalpa* spp., *Leucophaea maderae*, *Locusta* spp., *Periplaneta* spp. and *Schistocerca* spp.;

from the order Isoptera, for example, *Reticulitermes* spp.;

from the order Psocoptera, for example, *Liposcelis* spp.;

from the order Anoplura, for example, *Haematopinus* spp., *Linognathus* spp., *Pediculus* spp., *Pemphigus* spp. and *Phylloxera* spp.;

from the order Mallophaga, for example, *Damalinea* spp. and *Trichodectes* spp.;

from the order Thysanoptera, for example, *Frankliniella* spp., *Hercinothrips* spp., *Taeniothrips* spp., *Thrips palmi*, *Thrips tabaci* and *Scirtothrips aurantii*;

from the order Heteroptera, for example, *Dichelops melacanthus*, *Distantiella theobroma*, *Dysdercus* spp., *Euchistus* spp., *Eurygaster* spp., *Leptocorisa* spp., *Nezara* spp., *Piesma* spp., Rhodnius spp., *Sahlbergella singularis, Scotinophara* spp. and *Triatoma* spp.;

from the order Homoptera, for example, *Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;* from the order Hymenoptera, for example, *Acromyrmex, Athalia rosae, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;

from the order Diptera, for example, *Antherigona soccata, Bibio hortulanus, Ceratitis* spp., *Chrysomyia* spp., *Culex* spp., *Cuterebra* spp., *Dacus* spp., *Delia* spp., *Drosophila melanogaster, Liriomyza* spp., *Melanagromyza* spp., *Orseolia* spp., *Oscinella frit, Pegomyia hyoscyami, Phorbia* spp., *Rhagoletis pomonella, Sciara* spp.;

from the order Acarina, for example, *Acarus siro, Aceria sheldoni, Aculus schlechtendali, Amblyomma* spp., *Argas* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.; and from the class Nematoda, for example, the species of *Meloidogyne* spp. (for example, *Meloidogyne incoginita* and *Meloidogyne javanica*), *Heterodera* spp. (for example, *Heterodera glycines, Heterodera schachtii, Heterodora avenae* and *Heterodora trifolii*), *Globodera* spp. (for example, *Globodera rostochiensis*), *Radopholus* spp. (for example, *Radopholus similes*), *Rotylenchulus* spp., *Pratylenchus* spp. (for example, *Pratylenchus neglectans* and *Pratylenchus penetrans*), *Aphelenchoides* spp., *Helicotylenchus* spp., *Hoplolaimus* spp., *Paratrichodorus* spp., *Longidorus* spp., *Nacobbus* spp., *Subanguina* spp. *Belonlaimus* spp., *Criconemella* spp., *Criconemoides* spp. *Ditylenchus* spp., *Dolichodorus* spp., *Hemicriconemoides* spp., *Hemicycliophora* spp., *Hirschmaniella* spp., *Hypsoperine* spp., *Macroposthonia* spp., *Melinius* spp., *Punctodera* spp., *Quinisulcius* spp., *Scutellonema* spp., *Xiphinema* spp., and *Tylenchorhynchus* spp.

Examples of fungal pathogens includes seedborne and soilborne diseases, such as *Alternaria* spp., *Ascochyta* spp., *Botrytis cinerea, Cercospora* spp., *Claviceps purpurea, Cochliobolus sativus, Colletotrichum* spp., *Epicoccum* spp., *Fusarium graminearum, Fusarium moniliforme, Fusarium oxysporum, Fusarium proliferatum, Fusarium solani, Fusarium subglutinans, Gaumannomyces graminis, Helminthosporium* spp., *Microdochium nivale, Penicillium* spp., *Phoma* spp., *Pyrenophora graminea, Pyricularia oryzae, Rhizoctonia solani, Rhizoctonia cerealis, Sclerotinia* spp., *Septoria* spp., *Sphacelotheca reilliana, Tilletia* spp., *Typhula incarnata, Urocystis occulta, Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

A single pesticide may have activity in more than one area of pest control, for example, a pesticide may have fungicide, insecticide and nematicide activity. Specifically, aldicarb is known for insecticide, acaricide and nematicide activity, while metam is known for insecticide, herbicide, fungicide and nematicide activity, and thiabendazole and captan can provide nematicide and fungicide activity.

A pesticide may be used either in pure form, i.e., as a solid technical active ingredient, for example, in a specific particle size, or preferably together with at least one of the auxiliary (also known as adjuvants) customary in formulation technology, such as extenders, e.g., solvents or solid carriers, or surface-active compounds (surfactants), in the form of a pesticidal composition (as defined in the third aspect).

Whereas commercial pesticidal compositions or products will preferably be formulated as concentrates (known as a pre-mix composition (or concentrate, formulated compound (or product)), the end user (e.g., farmer, grower or plant propagation material treater) will normally employ them after dilution with a solvent (such as water), optionally also containing one or more other pesticide pre-mixes and formulation auxiliaries. The diluted version of the pesticidal compositions is known as a tank mix composition (or ready-to-apply, spray broth, or slurry). The end user of the pesticidal composition can also use the commercial pesticidal compositions without further dilution in certain circumstances. Accordingly, a pesticidal composition as used herein refers to a pre-mix composition or a tank mix composition. In a preferred embodiment, the pesticidal composition is a pre-mix composition.

In the event the pesticidal composition for use on the agronomic plants or propagation material thereof has pesticidal particles in the form of an emulsion droplet, the corresponding pre-mix for such a pesticidal composition may be (i) an emulsifiable concentrate, which on appropriate agitation with a second liquid forms the desired emulsion droplet in the pesticidal composition, or (ii) an emulsion composition, which may be in a concentrated form.

Therefore, formulation types of a pre-mix composition, which already contain the desired particle size, especially pesticide particle size, are a suspension formulation, capsule formulation, granule formulation or emulsion formulation. Thereafter the use of such pre-mix compositions on the agronomic plants or propagation material thereof may be with or without any dilution of the pre-mix composition by the end user.

In an embodiment of any one of the aspects of the present invention, the pesticidal composition is a plant propagation material, preferably seed, treatment composition or a soil application composition. A skilled person would understand how a plant propagation material, preferably seed, treatment composition or a soil application composition would be modified for its particular use.

The spectrum of pest control can be broadened and effectiveness of the pest control can be enhanced by use of one or more pesticides, such as insecticidally, acaricidally, nematicidally and/or fungicidally active compounds.

Accordingly, the pesticidal compositions of any one of the aspects of the invention, independently of each other, can have (1), (2), (3) or any combination thereof:

(1) two more pesticides (A), for example, abamectin and bifenthrin. In that event, the particle size of each pesticide (A) is independent of each other(s), but each pesticide (A) has the particle size as defined in any one of the aspects;

(2) one or more further pesticides (B) different from pesticide (A), which pesticide (B) independently of pesticide (A) has a particle size as defined in any one of the aspects;

(3) one or more additional pesticides (C), which do not have a particle size as defined in any one of the aspects, i.e., have a particle size different to that defined for pesticide (A) or pesticide (B) (i.e, the size of particles is not in the range 3.60 µm to 0.70 µm, preferably 3.40 µm to 0.80 µm, more preferably 2.60 µm to 1.2 µm, most preferably 2.00 µm to 1.50 µm).

Therefore, a pesticidal composition (either a pre-mix composition or tank-mix composition) may comprise the pesticides defined in (1), (2), (3) or any combination thereof.

Further, the spectrum of pest control can be broadened and effectiveness of the pest control can be enhanced by use of a second pesticidal composition comprising, as active ingredient, one or more pesticides (D), wherein pesticide (D) can be pesticide (A), (B) and (C) as defined herein. The second pesticidal composition can be applied or treated simultaneously or sequentially with the pesticidal composition defined in any one of the aspects. In the event it is used (applied or treated) simultaneously, a third pesticidal composition may be obtained comprising the pesticidal composition defined in any one of the aspects and the second pesticidal composition; in such an event the third pesticidal composition would be a tank-mix composition. In the event it is used sequentially, the order of use is not critical and the compositions do not need to be used immediately after each other.

A particular advantage of the present invention is that the same pesticide compound may be present in a pesticidal composition for different purposes because different particle sizes of that pesticide are present for optimised pest management, such as different pesticide particle size may provide delayed release of its biological activity, or different pesticide particle sizes may provide activity against different pests—so it is envisaged, for example, that the same pesticide compound is present as pesticide (A) and pesticide (C).

In an embodiment, the pesticidal composition of any one of the aspects consists essentially of, as active ingredient, pesticide (A).

Examples of pesticide (B) that have a particle size as defined in any one of the aspects (i.e., size of particles in the range 3.60 µm to 0.70 µm, preferably 3.40 µm to 0.80 µm, more preferably 2.60 µm to 1.2 µm, most preferably 2.00 µm to 1.50 µm) are azoxystrobin; bitertanol; carboxin; $Cu_2O$; cymoxanil; cyproconazole; cyprodinil; dichlofluamid; difenoconazole; diniconazole; epoxiconazole; fenpiclonil; fludioxonil; fluquinconazole; flusilazole; flutriafol; furalaxyl; guazatin; hexaconazole; hymexazol; imazalil; imibenconazole; ipconazole; kresoxim-methyl; mancozeb; metalaxyl; R-metalaxyl; metconazole; oxadixyl; pefurazoate; penconazole; pencycuron; prochloraz; propiconazole; pyroquilone; spiroxamin; tebuconazole; thiabendazole; tolifluamide; triazoxide; triadimefon; triadimenol; triflumizole; triticonazole; uniconazole; (±)-cis -1-(4-chlorophenyl)-2-(1H -1,2,4-triazol-1-yl)cycloheptanol); prothioconazole; thiram; carbendazim; PCNB (quintozene); TCMTB (2-(thiocyanatomethylthio)benzothiazole); benalaxyl; benalaxyl-M; silthiofam; fluoxastrobin; chloroneb; emamectin; acetamiprid; nitenpyram; chlothianidin; dinotefuran; fipronil; thiacloprid; thiodicarb; spinosad; imidacloprid; thiamethoxam; and tefluthrin.

Pesticide (C) can be a pesticide selected from the pesticide (A) and (B), but does not have the particle size as defined in any one of the aspects of the invention.

Pesticide (D) can be a pesticide selected from the pesticide (A), (B) and (C), which has or has not the particle size as defined in any one of the aspects.

Specific examples of pesticide combinations are abamectin and one or more of thiamethoxam, imidacloprid, clothianidin, tefluthrin, beta-cyfluthrin, beta-cypermethrin, theta-cypermethrin, zeta-cypermethrin, thiram, benalaxyl, benalaxyl-M, fuberdiazole, thiabendazole, azoxystrobin, fluoxastrobin, bitertanol, cyproconazole, difenoconazole, diniconazole, myclobutanil, fluquinconazole, flutriafol, metalaxyl, metalaxyl-M, prothioconazole, tebuconazole, triadimenol, triticonazole, fludioxonil, triazoxide, cyprodinil, carboxin, chloroneb, PCNB (quintozene); TCMTB (2-(thiocyanatomethylthio)benzothiazole); and silthiofam. Also envisaged is the use of a chelating agents with abamectin; chelating agents are in metallated form (a metal cation is entrapped or sequestered by the chelating agent), or in the unmetallated form (no metal cation or another compound is sequestered, or another non-metal compound is sequestered) and examples include iron chelates of a EDDHA, such as (o,o-EDDHA), (o,p-EDDHA), (p,p-EDDHA), or a mixture thereof.

In an embodiment, the pesticidal composition comprises, as active ingredient, abamectin, a neonicotinoid (such as thiamethoxam or imidicloprid), azoxystrobin, fludioxonil, metalxyl-M, myclobutanil, and optionally difenoconazole, where abamectin is pesticide (A), and the remaining active ingredients can be, independently of each other, either pesticide (B) or (C).

The pesticidal compositions can take a variety of forms and are generally specifically formulated for its application, for example, plant propagation material treatment, foliar application and soil application.

Examples Of Seed Treatment Pre-mix Composition Or Formulation Types Are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

The tank-mix compositions or formulations are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

The formulations are prepared in known manner, e.g., by homogeneously mixing and/or grinding the active ingredients with extenders, e.g., solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g., for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g., especially dolomite or pulverized plant residues.

Depending upon the nature of the pesticide(s) to be formulated, suitable surface-active compounds are non-ionic, cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g., phosphatidylethanolamine, phosphatidylserine, phosphatidylglycerol and lysolecithin.

Generally, a tank-mix formulation for soil application comprises 0.1 to 20%, especially 0.1 to 15%, pesticide(s), and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for soil application comprises 0.1 to 99.9%, especially 1 to 95%, pesticide(s), and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for plant propagation material, preferably seed, treatment application comprises 0.25 to 80%, especially 1 to 75%, pesticide(s), and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for plant propagation material, preferably seed, treatment application comprises 0.5 to 99.9%, especially 1 to 95%, pesticide(s), and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

In one embodiment, the pesticide (or active ingredient) is present in the pesticidal composition of any one of the aspects in an amount of from about 12.5% to about 60% by weight, more specifically, from 30 to about 55%, such as 40 to 55%, by weight of the composition; the balance of the composition, also known as a formulation, comprising a water along with surfactant(s) and other optional inert ingredients known in the art as formulation adjuvants, e.g., protective colloids, adhesives, thickeners, thixotropic agents, penetrating agents, preservatives, stabilizers, antifoaming agents, antifreeze agents, sequestering agents, colourings, such as dyes or pigments, and polymers.

In an embodiment, at least two surface active compounds (designated herein as (β)) are present in the pesticidal composition, such as a pre-mix composition: (i) at least one is surface active compound having a molecular weight of less than 2200, preferably less than 1700, such as in the range 400 to 1500, advantageously in the range 600 to 1200, and a Hydrophile-Lipophilic Balance (HLB) of at least 10, preferably in the range 10 to 25, such as 12 to 20, preferably 14 to 18; and (ii) at least one surface active compound is non-ionic, has a molecular weight of at least 2200, preferably at least 3000, such as in the range of 3500 to 15000, for example, 3500 to 10000, especially 4000 to 7500, advantageously 4500 to 6000, wherein 10 to 60, such as 15 to 55, preferably 17 to 50,%, of the compound molecular weight contributes to the hydrophile constituent of the compound, and the molecular weight of the hydrophobe constituent of the compound is from 2000 to 10000, preferably 2400 to 3900, more preferably 3000 to 3800, such as 3200 to 3700.

In an embodiment, the pesticidal composition according to any one of the aspects is a composition, comprising (α) a pesticide (A) and optionally at least one other substance which has a melting point above 30° C., such as a pigment.

In a preferred embodiment, the pesticidat composition according to any one of the aspects is an aqueous suspension composition, comprising a pesticide (A), preferably abamectin, wherein the weight ratio of (β):(α) is in the range 0.08 to 0.5, preferably 0.1 to 0.3, advantageously 0.15 to 0.25, and the weight ratio of (β)(ii):(β)(i) is at least 0.5, such as at least 1.0, preferably at least 1.5, especially in the range 2 to 5, advantageously in the range 2 to 3.

The amount of surface active compounds (β) generally present range from 1 to 25, preferably 2.4 to 22.5, especially 5 to 10,%, by weight, based on the weight of the composition of the first aspect. Surface active compounds are made up of water soluble (hydrophilic) groups (or constituents), such as polyoxyethylene, and water insoluble (hydrophobic) groups (or constituents), such as polyoxypropylene. Examples of surface active compounds are surfactants having good emulsifying, dispersing and wetting properties, depending on the nature of the pesticide to be formulated. Surfactants will also be understood as meaning mixtures of surfactants. Surfactants are non-ionic, cationic and/or anionic.

The (β)(i) surface active compound preferably has a molecular weight of at least 100.

The (β)(ii) surface active compound preferably has a molecular weight of at most of 100,000.

In an embodiment, the weight ratio of surface active compounds (ii) to (i) is at most 10.

In an embodiment, two surface active compounds (β)(ii) are present in the composition.

In the event, two surface active compounds (β)(ii) are present:
the first surface active compound has a molecular weight of the hydrophobe constituent of from 2400 to 3900, preferably 3000 to 3800, such as 3200 to 3700 and, independent of the hydrophobe molecular weight, a proportion of the molecular weight of the hydrophile constituent of from 13 to 45, preferably 17 to 40, such as 18 to 30,%; and
the second surface active compound has a molecular weight of the hydrophobe constituent of from 2200 to 3900, preferably 2500 to 3600, such as 2700 to 3200 and, independent of the hydrophobe molecular weight, a proportion of the molecular weight of the hydrophile constituent of from 43 to 67, preferably 45 to 65, such as 50 to 60,%.

The Hydrophile-Lipophilic Balance (HLB) value is an index of the hydrophilic nature of a compound proposed by Griffin. The HLB value of a polyoxyethylene alkyl ether can be determined by, for example, the Griffin equation.

HLB value=[(molecular weight of the hydrophilic moiety)/(molecular weight of the surface active compound)]×20

Generally, compounds, including surface active compounds, that are commercially used tend to be not analytically pure, but a mixture of suitable compounds, for example, of the same chemistry but of different analogs, isomers and molecular weights. The characteristics attributed to, for example, the (β)(i) and (β)(ii) surface active compounds are, therefore, preferably also satisfied in a mixture of compounds where the characteristics are possessed by a compound in the mixture, which compound is present in a major proportion, such as greater than 50, preferably greater than 60, especially greater than 75,% by weight, based on the weight of the mixture; more preferably, the mixture itself satisfies the characteristics defined.

In an embodiment, the (β)(i) surface active compound is an ionic, advantageously an anionic, surfactant; preferably one or more (β)(i) surface active compound is selected from a sulfate type (e.g., an aryl sulfate) and a phosphate type (such as an alkylphenol polyalkoxyether phosphate, a block copolymer of polyalkoxyether phosphate, polyarylphenol polyalkoxyether phosphate and an arylphenol polyalkoxyether phosphate), especially a phosphate type surfactant (such as a polyarylphenol polyalkoxyether phosphate). Particularly desired in the compositions of the invention are that each (β)(i) surface active compound is of the same type, a preferred type is a phosphate type surfactant.

The anionic surfactants may be present as acids or include alkali metals (such as lithium, sodium and potassium), alkali earth metals (such as calcium and magnesium), ammonium and various amines (such as alkylamines, cycloalkylamines and alkanolamines).

Specific examples of suitable anionic surfactants include: Soprophor PS19 (Rhodia), Dowafax 30 C05 (Dow), Soprophor 4D384 (Rhodia) and Soprophor 3D33 (Rhodia).

In an embodiment, the (β)(ii) surface active compound is a polyalkylene oxide polymer, such as a block polymer. Specific examples are polyoxyethylene polyoxypropylene block polymers, and polyoxyethylene polyoxypropylene block polymer ethers. Specific examples include Toximul 8320 (Stepan), Emulsogen 3510 (Clariant), Antarox PL/122 (Rhodia), Pluronic L101 (BASF), Pluronic L122 (BASF) and Pluronic PE 10500 (BASF).

The pesticidal compositions can also contain a wetting agent, which is also considered surface active compound in that it has a water soluble (hydrophilic) and water insoluble (hydrophobic) components, but they tend to non-ionic and generally have a molecular weight of less than 2000, and so can be a component according to (B)(i); a wetting agent, however, is not generally present.

The pesticidal compositions can be employed together with the adjuvants customary in formulation technology, biocides, biostats, anti-thickening agent, anti-freeze, emulsifiers (lethicin, sorbitan, and the like), antifoam agents or application-promoting adjuvants customarily employed in the art of formulation. In addition, there may be mentioned inoculants and brighteners.

Additionally, a colouring agent, such as a dye or pigment, is included in the seed coating so that an observer can immediately determine that the seeds are treated. The colouring agent is also useful to indicate to the user the degree of uniformity of the coating applied. Generally, the colouring agent tends to have a melting point above 30° C., and therefore, is also suspended in the compositions of the present invention.

The pesticidal compositions can be prepared by processes known in the art, such as forming a homogeneous suspension with all the components, except the thickeners, and wet milling the suspension until the desired particle size is reached, then the thickeners and further water are added to a set viscosity.

The final composition can be screened if desired to remove any insoluble particles of the undesired particle size.

The Examples, Which Follow Serve To Illustrate The Suitable Formulations Are:

| Wettable powders | a) | b) | c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Dusts | a) | b) | c) |
|---|---|---|---|
| active ingredient | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can be used for dry dressings for seed.

| Suspension concentrates | (a) | (b) |
|---|---|---|
| active ingredient | 5% | 30% |
| propylene glycol | 10% | 10% |
| Tristyrylphenol ethoxylates | 5% | 6% |
| sodium lignosulfonate | — | 10% |
| carboxymethylcellulose | — | 1% |
| silicone oil (in the form of a 75% emulsion in water) | 1% | 1% |
| Colour pigment | 5% | 5% |
| water | 74% | 37% |

The finely ground active ingredient is intimately mixed with the adjuvants, giving a suspension concentrate from which suspensions of any desired dilution can be obtained by dilution with water. Alternatively, a suspension of the active ingredients and auxiliaries (including water) is wet milled with a bead-mill to achieve a stable formulation and with the appropriate treatment characteristics.

Using such formulations, either straight or diluted, plant propagation material can be treated and protected against damage, for example, from pathogen(s), by, for example, spraying, pouring or immersing.

The active ingredient combinations according to the invention are distinguished by the fact that they are especially well tolerated by plants and are environmentally friendly.

The compositions of the invention are formulated for protecting cultivated plants and their propagation materials. The compositions are advantageously formulated for seed treatment applications against soil-dwelling pests and/or soil-borne diseases, such as animal pests (in particular insects, arachnids and nematodes) and fungal pathogens, which are found in agriculture and forestry, and can particularly damage the plant in the early stages of its development.

Further, the present invention also envisages soil application of the compositions of the invention to control the soil-dwelling pests and/or soil-borne diseases.

The benefit from the invention can be achieved either by (i) treating plant propagation material with the defined pesticide particles in a suitable form or (ii) applying to the locus where control is desired, generally the planting site, the defined pesticide particles in a suitable form, or both (i) and (ii).

Methods for applying pesticides on to plant propagation material, especially seeds, are known in the art, and include dressing, coating, pelleting and soaking application methods of the propagation material.

It is preferred that the plant propagation material is a seed. Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the active ingredients and adherence thereof to the seeds is desired during propagation material treatment. Treatment could vary from a thin film (dressing) of the formulation containing the active ingredient(s) on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the pesticide is applied to the soil but would include any application practice that would target the seed during the planting process.

Preferably, the treatment occurs before sowing of the seed so that the sown seed has been pre-treated with the defined pesticide particles. In particular, seed coating or seed pelleting are preferred in the treatment of the combinations according to the invention. As a result of the treatment, the pesticide particles are adhered on to the seed and therefore available for pest control.

The treated seeds can be stored, handled, sowed and tilled in the same manner as any other pesticide treated seed.

The amount used on the propagation material varies according to specific active ingredient (e.g., abamectin is generally applied at a lower rate than lambda-cyhalothrin, type of propagation material (e.g., seed or tuber) and plant (for example, wheat seeds generally have less active ingredients adhered thereto than oil seed rape seeds based on equivalent weight of seeds) and is such that the defined pesticide particles is an effective amount to provide the desired pesticidal action and can be determined by biology trials.

The application rates can, therefore, range from 6 g to 250 kg of per 100 kg of seeds. Generally, the application rate for cereal seeds range from 23 g to 740 g, preferably 50 g to 600 g, per 100 kg of seeds; and the application rate for oil seed rape seeds can range from 700 g to 25 kg, preferably 1.5 kg to 20 kg, per 100 kg of seeds. Generally treatment rate of abamectin on to a cotton seed is in the range of 0.1 to 0.2 mg ai/seed, to a tomato seed is in the range of 0.3 to 0.6 mg ai/seed and to a soybean seed is in the range of 0.1 to 0.2 mg ai/seed.

Therefore, the present invention also provides a plant propagation material treated with the pesticidal composition or pesticide of the third or fourth aspect respectively. At least the defined pesticides, and optionally certain formulation auxiliaries, are adhered on to the plant propagation material, and accordingly, the plant propagation material comprises the defined pesticides.

The pesticide particles in a suitable form can also be applied to the locus where control of soil-dwelling pests and/or soil-borne pathogens is desired, generally at location where growth of the plant occurs. This may be carried out on one or more occasions during the growth of the plant (e.g. pre-emergence and/or post-emergence), before it is planted or sown or during its planting or sowing and any combination thereof.

The use of the pesticide particles in a suitable form can be via any suitable method, which ensures that the pesticide particles penetrates the soil, for example, nursery tray application, in furrow application, soil drenching, soil injection, drip irrigation, application through sprinklers or central pivot, incorporation into soil (broad cast or in band) are such methods.

The rate and frequency of use of the pesticide particles in a suitable from on the plant may vary within wide limits and depends on the type of use, the specific pesticide, the nature of the soil, the method of application (pre- or post-emergence, etc.), the plant or pest to be controlled, the prevailing climatic conditions, and other factors governed by the method of application, the time of application and the target plant.

Typical application rate of abamectin to the locus of the crop plant is from 3 to 90 g per hectare (g/ha), especially from 6 to 60 g/ha, preferably from 9 to 36 g/ha, most preferably from 12 to 27 g/ha. The pesticide may be applied once or several occasions during the growth of a plant depending on the plant and circumstances, for example, 1 to 6 or 1 to 4 occasions (for a tomato crop harvest, for example, the combination can be applied up to 6 times before harvest), and the amounts indicated above are for each application.

It is anticipated that the present invention also extends to control of soil-dwelling pests and/or soil-borne diseases through the combined methods of plant propagation material treatment and soil application at the locus of the planting or sowing.

The present invention is especially found to show an improvement in the growing characteristics of a plant; in the instance abamectin is pesticide (A), the invention provides an improved control against nematodes, and thus improves the growing characteristics of the plant.

The improvement in the growing (or growth) characteristics of a plant can manifest in a number of different ways, but ultimately it results in a better product of the plant. It can, for example, manifest in improving the yield and/or vigour of the plant or quality of the harvested product from the plant.

As used herein the phrase "improving the yield" of a plant relates to an increase in the yield of a product of the plant by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. Yield can be expressed in terms of an amount by weight or volume of a product of the plant on some basis. The basis can be expressed in terms of time, growing area, weight of plants produced, amount of a raw material used, or the like.

As used herein the phrase "improving the vigour" of a plant relates to an increase or improvement of the vigour rating, or the stand (the number of plants per unit of area), or the plant height, or the plant canopy, or the visual appearance (such as greener leaf colour), or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method.

When it is said that the present method is capable of "improving the yield and/or vigour" of a plant, the present method results in an increase in either the yield, as described above, or the vigor of the plant, as described above, or both the yield and the vigor of the plant.

In an embodiment, the pesticidal composition according to the invention can also be used to treat stored products, such as grain, for protection against pathogens and/or pests.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The pesticides having a common name are described in the e-Pesticide Manual, version 3.0, 13th Edition, Ed. CDC Tomlin, British Crop Protection Council, 2003-04, along with their characteristics.

The following Examples are given by way of illustration and not by way of limitation of the invention.

EXAMPLES

Examples A and 1 to 6 are prepared by mixing surfactants (strylphenol polyethoxyether phosphate, PO-EO block copolymer, butyl-capped PO-EO copolymer), neutraliser, a defoaming agent, an antifreeze agent, and a bactericide with water until a homogeneous phase is achieved. Subsequently, a colour pigment and abamectin, which had been already air-jet milled to a predetermined particle size, are added and are mixed. The resulting mixture is then wet-milled through a so-called bead mill (Dyno, Drais, Premier for instance) and samples taken over time from the mixture, and a thickening agent and a minor amount of water are added and each resulting sample is mixed for at least 30 minutes to provide Examples A and 1 to 6 (see Table 2).

Table 2 indicates the particle size details of Examples A and 1 to 6, with each composition containing identical amounts of active ingredient, & formulation auxiliaries, such as surfactants, pigment, defoaming agent, thickener and bactericide.

Maize seeds are cauterized, to prevent them from germinating, and are treated with Examples A and 1 to 6 at a rate of 0.6 mg of abamectin/seed. Seeds are placed into plastic columns filled with sand, one seed per column. Columns are then watered with a total of 240 mL tap water spread over 11 days. Thereafter, the columns are cut into 5-cm segments. The sand from each segment is placed into a pot and a cucumber seedling, used as an indicator plant, is planted into the substrate of each segment and inoculated with 3000 eggs of Meloidogyne incognita. Cucumber plants are assessed after 14 days and the root galling is determined on each plant.

The average nematicidal efficacy in the upper 10 cm of the sand column (compared to untreated seedlings) is provided in Table 2 for each example:

TABLE 2

| Example | Particle size*, $x_{90}$ | efficacy (%) |
|---------|--------------------------|--------------|
| A | 5.39 μm | 60.0 |
| 1 | 3.31 μm | 45.2 |
| 2 | 2.53 μm | 56.5 |
| 3 | 1.83 μm | 73.5 |
| 4 | 1.29 μm | 68.7 |
| 5 | 0.98 μm | 65.7 |
| 6 | 0.84 μm | 64.8 |

*as measured by ISO 13320-1: 1999

The invention claimed is:

1. A method for achieving an improvement in plant growth characteristics, the method comprising:
   treating a plant propagation material with a pesticidally effective amount of a composition comprising abamectin particles and at least one formulation auxiliary, and
   planting or sowing the plant propagation material either after or during the treatment of the pesticidal composition; and
   wherein the size of the size of the abamectin particles in the composition is in the range 2.00 μm to 0.80 μm at $x_{90}$ as defined in ISO 13320-1.

2. A method of protecting plant propagation material and plant organs that grow at a later point in time, which comprises treating the plant propagation material with a pesticidally effective amount of a pesticidal composition comprising abamectin particles having a water solubility of at most 100 μg/liter at 25° C. at neutral pH, and at least one formulation auxiliary, wherein the size of the abamectin particles in the composition is in the range 2.00 μm to 0.80 μm at $x_{90}$ as defined in ISO 13320-1.

3. A method for the control of soil-dwelling pests and/or soil-borne diseases comprising treating a plant propagation material with a pesticidally effective amount of the pesticidal composition and/or applying an effective amount of a pesticidal composition to a locus where control is desired, provided that the composition comprises abamectin particles having a water solubility of at most 100 μg/liter at 25° C. at neutral pH, and at least one formulation auxiliary, wherein the size of the abamectin particles in the composition is in the range 2.00 μm to 0.80 at $x_{90}$ as defined in ISO 13320-1.

4. The method according to claim 1 wherein the composition is in the form of a suspension.

5. The method according to claim 1 wherein the plant is selected from cotton, corn, cereals, vegetables, clovers, legumes, sugar cane, sugar beets, tobacco, rapeseed, fruits, perennial crops, deciduous plants, sunflower, safflower, and sorghum.

6. The method according to claim 5 wherein the plant is a genetically modified plant containing one or more genes expressing pesticidal resistance.

7. The method according to claim 1 wherein the treatment of the plant propagation material is before the plant propagation material is sown or planted in the soil or is during the planting or sowing of the plant propagation material.

8. The method according to claim 1 wherein the composition further comprises an additional pesticide.

9. The method according to claim 1 wherein the composition also comprises an additional pesticide, wherein the size of each of a particle of each additional pesticide is <0.70 μm and/or >3.60 μm at $x_{90}$ as defined in ISO 13320-1.

10. The method according to claim 8, wherein the additional pesticide is selected from azoxystrobin; bitertanol; carboxin; $Cu_2O$; cymoxanil; cyproconazole; cyprodinil; dichlofluamid; difenoconazole; diniconazole; epoxiconazole; fenpiclonil; fludioxonil; fluquiconazole; flusilazole; flutriafol; furalaxyl; guazatin; hexaconazole; hymexazol; imazalil; imibenconazole; ipconazole; kresoxim-methyl; mancozeb; metalaxyl; R-metalaxyl; metconazole; oxadixyl; pefurazoate; penconazole; pencycuron; prochloraz; propiconazole; pyroquilone; spiroxamin; tebuconazole; thiabendazole; tolifluamide; triazoxide; triadimefon; triadimenol; triflumizole; triticonazole; uniconazole; (±)-cis -1-(4-chlorophenyl)-2-(1H -1,2,4-triazol-1-yl) cycloheptanol); prothioconazole; thiram; carbendazim; PCNB (quintozene); TCMTB (2-(thiocyanatomethylthio)benzothiazole); benalaxyl; benalaxyl-M; silthiofam; fluoxastrobin; chloroneb; emamectin; acetamiprid; nitenpyram; chlothianidin; dinotefuran; fipronil; thiacloprid; thiodicarb; spinosad; imidacloprid; thiamethoxam; and tefluthrin.

11. A pesticidal composition comprising, as active ingredient, abamectin particles having a water solubility of at most 100 μg/liter at 25° C. at neutral pH, and at least one formulation auxiliary, wherein the size of the abamectin particles in the composition is in the range 2.00 μm to 0.80 μm at $x_{90}$ as defined in ISO 13320-1.

12. A method for achieving an improvement in plant growth characteristics, the method comprising:
    treating a plant propagation material with a pesticidally effective amount of a composition comprising abamectin particles and at least one formulation auxiliary, and
    planting or sowing the plant propagation material either after or during the treatment of the pesticidal composition; and
    wherein the abamectin particles have a water solubility of at most 100 μg/liter at 25° C. at neutral pH and the size of the size of the abamectin particles in the composition is in the range 2.00 μm to 0.80 μm at $x_{90}$ as defined in ISO 13320-1.

13. A method for controlling soil dwelling pests and/or soil borne diseases, the method comprising:
    treating a plant propagation material with a pesticidally effective amount of a composition comprising abamectin particles and at least one formulation auxiliary, and
    planting or sowing the plant propagation material either after or during the treatment of the pesticidal composition; and
    wherein the size of the size of the abamectin particles in the composition is in the range 2.00 μm to 0.80 μm at $x_{90}$ as defined in ISO 13320-1.

14. The method according to claim 1 wherein plant propagation material is planted or sown in a soil type selected from sandy clay, sandy clay loam, sandy loam, loamy sand and sand.

15. A plant propagation material treated with the pesticidal composition defined in claim 11.

\* \* \* \* \*